(12) United States Patent
Cunningham et al.

(10) Patent No.: US 9,393,197 B2
(45) Date of Patent: Jul. 19, 2016

(54) STABLE EMULSION FOR PREVENTION OF SKIN IRRITATION AND ARTICLES USING SAME

(71) Applicant: Kimberly-Clark Worldwide, Inc., Neenah, WI (US)

(72) Inventors: Corey Thomas Cunningham, Larsen, WI (US); Jeffery Richard Seidling, Appleton, WI (US); Lisa Marie Kroll, Appleton, WI (US); Stacy Averic Mundschau, Weyauwega, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 348 days.

(21) Appl. No.: 13/925,788

(22) Filed: Jun. 24, 2013

(65) Prior Publication Data

US 2014/0004166 A1    Jan. 2, 2014

Related U.S. Application Data

(60) Provisional application No. 61/666,407, filed on Jun. 29, 2012.

(51) Int. Cl.
| | |
|---|---|
| *A61K 9/107* | (2006.01) |
| *A61K 31/695* | (2006.01) |
| *A61K 35/02* | (2015.01) |
| *A61K 8/26* | (2006.01) |
| *A61K 8/60* | (2006.01) |
| *A61K 8/73* | (2006.01) |
| *A61K 8/81* | (2006.01) |
| *A61Q 19/00* | (2006.01) |
| *A61K 8/86* | (2006.01) |
| *A61Q 19/10* | (2006.01) |
| *A61K 8/891* | (2006.01) |
| *A61K 8/02* | (2006.01) |

(52) U.S. Cl.
CPC ............... *A61K 9/107* (2013.01); *A61K 8/0208* (2013.01); *A61K 8/26* (2013.01); *A61K 8/602* (2013.01); *A61K 8/733* (2013.01); *A61K 8/8158* (2013.01); *A61K 8/86* (2013.01); *A61K 8/891* (2013.01); *A61K 31/695* (2013.01); *A61K 35/02* (2013.01); *A61Q 19/005* (2013.01); *A61Q 19/10* (2013.01)

(58) Field of Classification Search
None
See application file for complete search history.

(56) References Cited

U.S. PATENT DOCUMENTS

| | | |
|---|---|---|
| 3,896,807 A | 7/1975 | Buchalter |
| 4,382,919 A | 5/1983 | Alonso et al. |
| 4,690,821 A | 9/1987 | Smith et al. |
| 4,772,501 A | 9/1988 | Johnson et al. |
| 4,806,572 A | 2/1989 | Kellett |
| 4,904,524 A | 2/1990 | Yoh |
| 5,110,593 A | 5/1992 | Benford |
| 5,362,488 A | 11/1994 | Sibley et al. |
| 5,385,748 A | 1/1995 | Bunger et al. |
| 5,436,007 A | 7/1995 | Hartung et al. |
| 5,525,346 A | 6/1996 | Hartung et al. |
| 5,585,104 A | 12/1996 | Ha et al. |
| 5,643,588 A | 7/1997 | Roe et al. |
| 5,648,083 A | 7/1997 | Blieszner et al. |
| 5,858,335 A | 1/1999 | Lucas et al. |
| 5,861,145 A | 1/1999 | Lucas et al. |
| 5,861,147 A | 1/1999 | Dodd et al. |
| 5,863,663 A | 1/1999 | Mackey et al. |
| 5,874,067 A | 2/1999 | Lucas et al. |
| 5,968,025 A | 10/1999 | Roe et al. |
| 5,985,177 A * | 11/1999 | Yoshida ................. A61K 8/066 252/364 |
| 6,083,854 A | 7/2000 | Bogdanski et al. |
| 6,103,245 A | 8/2000 | Clark et al. |
| 6,153,208 A | 11/2000 | McAtee et al. |
| 6,280,757 B1 | 8/2001 | McAtee et al. |
| 6,287,581 B1 | 9/2001 | Krzysik et al. |
| 6,303,119 B1 | 10/2001 | Weisgerber et al. |
| 6,352,700 B1 | 3/2002 | Luu et al. |
| 6,410,039 B1 | 6/2002 | Walker |
| 6,416,788 B1 | 7/2002 | Barr |
| 6,419,963 B1 | 7/2002 | Niazi |
| 6,436,418 B1 | 8/2002 | Sheldon et al. |
| 6,440,437 B1 | 8/2002 | Krzysik et al. |
| 6,461,601 B1 | 10/2002 | Stoddart et al. |
| 6,488,943 B1 | 12/2002 | Beerse et al. |
| 6,500,443 B1 | 12/2002 | Otts et al. |
| 6,503,524 B1 | 1/2003 | Tyrrell et al. |
| 6,544,573 B1 | 4/2003 | Pajela et al. |
| 6,603,053 B2 | 8/2003 | Hisanaka |
| 6,638,527 B2 | 10/2003 | Gott et al. |

(Continued)

FOREIGN PATENT DOCUMENTS

| | | |
|---|---|---|
| EP | 0 117 613 B1 | 6/1990 |
| EP | 0 564 307 A1 | 10/1993 |

(Continued)

OTHER PUBLICATIONS

Runhe Sea Melody Wet Wipes, sold on Mintel web page "http://www.gnpd.com", Jun. 2010, 2 pages.

Kamath, M.G. et al., "Spunlace (Hydroentanglement)," Internet web page "http://www.engr.utk.edu/mse/Textiles/Spunlace.htm", Apr. 2004, pp. 1-19.

*Primary Examiner* — Jake Vu
(74) *Attorney, Agent, or Firm* — Kimberly-Clark Worldwide, Inc.

(57) ABSTRACT

An emulsion suitable for incorporation into wet wipes used to clean urine and fecal matter from the skin. The emulsion includes silicone oil and clay. Phase separation is prevented with an emulsification system that includes a gum blend and either a Gemini surfactant restrained to the oil phase or a glucoside-based emulsifier. The gum blend includes at least one gum and propylene glycol alginate.

19 Claims, No Drawings

(56) References Cited

U.S. PATENT DOCUMENTS

| | | | |
|---|---|---|---|
| 6,696,070 B2 | 2/2004 | Dunn | |
| 6,803,496 B2 | 10/2004 | Elder et al. | |
| 6,831,107 B2 | 12/2004 | Dederen et al. | |
| 6,894,028 B2 | 5/2005 | Lipton et al. | |
| 7,122,238 B2 | 10/2006 | Macedo | |
| 7,147,751 B2 | 12/2006 | Shannon et al. | |
| 7,169,400 B2 | 1/2007 | Luu et al. | |
| 7,195,771 B1 | 3/2007 | Hsu et al. | |
| 7,358,279 B2 | 4/2008 | Goget et al. | |
| 7,365,030 B2 | 4/2008 | Chamba et al. | |
| 7,416,735 B2 | 8/2008 | El-Nokaly et al. | |
| 7,592,019 B2 | 9/2009 | Drucks et al. | |
| 7,651,691 B2 * | 1/2010 | Roso | A61K 8/06 424/400 |
| 7,838,477 B2 | 11/2010 | Wenzel et al. | |
| 7,951,840 B2 | 5/2011 | Modak et al. | |
| 2002/0025334 A1 | 2/2002 | Smith | |
| 2002/0120242 A1 | 8/2002 | Tyrrell et al. | |
| 2002/0165508 A1 | 11/2002 | Klofta et al. | |
| 2003/0035785 A1 | 2/2003 | Palumbo et al. | |
| 2003/0045645 A1 | 3/2003 | Chang et al. | |
| 2003/0082223 A1 | 5/2003 | Healy et al. | |
| 2003/0124373 A1 | 7/2003 | Weuthen et al. | |
| 2003/0165449 A1 | 9/2003 | Kaczvinsky et al. | |
| 2003/0220042 A1 | 11/2003 | Lostocco et al. | |
| 2004/0052834 A1 | 3/2004 | West et al. | |
| 2004/0058073 A1 | 3/2004 | Bunyard et al. | |
| 2004/0122389 A1 | 6/2004 | Mace et al. | |
| 2004/0166183 A1 | 8/2004 | Ruseler-Van et al. | |
| 2004/0242097 A1 | 12/2004 | Hasenoehrl et al. | |
| 2005/0002994 A1 | 1/2005 | Goppel et al. | |
| 2005/0008680 A1 | 1/2005 | Deckner et al. | |
| 2005/0008681 A1 | 1/2005 | Deckner et al. | |
| 2005/0013790 A1 | 1/2005 | Yamaki et al. | |
| 2005/0031653 A1 | 2/2005 | Kwetkat et al. | |
| 2005/0031847 A1 | 2/2005 | Martens et al. | |
| 2005/0036960 A1 | 2/2005 | Bussey et al. | |
| 2005/0048105 A1 | 3/2005 | McNulty et al. | |
| 2005/0058672 A1 | 3/2005 | Gupta | |
| 2005/0158369 A1 | 7/2005 | Dorschner et al. | |
| 2006/0159645 A1 | 7/2006 | Miller et al. | |
| 2006/0171971 A1 | 8/2006 | Marsh et al. | |
| 2006/0193819 A1 | 8/2006 | Lu et al. | |
| 2006/0210612 A1 | 9/2006 | Simon et al. | |
| 2007/0020342 A1 | 1/2007 | Modak et al. | |
| 2007/0141127 A1 | 6/2007 | Casas-Sanchez et al. | |
| 2007/0254543 A1 | 11/2007 | Bunyard et al. | |
| 2008/0145664 A1 | 6/2008 | Sirovatka et al. | |
| 2008/0146484 A1 | 6/2008 | Sirovatka et al. | |
| 2008/0207767 A1 | 8/2008 | Dobos et al. | |
| 2008/0299065 A1 | 12/2008 | Arditty | |
| 2009/0035229 A1 | 2/2009 | Eirew | |
| 2009/0035340 A1 | 2/2009 | Landa et al. | |
| 2009/0081269 A1 * | 3/2009 | Erazo-Majewicz | A61K 8/0208 424/409 |
| 2009/0181070 A1 | 7/2009 | Blease et al. | |
| 2009/0226498 A1 | 9/2009 | Flugge-Berendes et al. | |
| 2009/0263439 A1 | 10/2009 | Casas-Sanchez et al. | |
| 2010/0158964 A1 | 6/2010 | Cunningham et al. | |
| 2011/0033413 A1 | 2/2011 | Kwetkat et al. | |
| 2011/0224637 A1 | 9/2011 | Edgett et al. | |
| 2011/0268777 A1 | 11/2011 | Marsh et al. | |
| 2011/0318434 A1 | 12/2011 | Guthery | |
| 2012/0090113 A1 | 4/2012 | Manifold et al. | |
| 2014/0004163 A1 | 1/2014 | Mundschau et al. | |
| 2014/0004164 A1 | 1/2014 | Mundschau et al. | |

FOREIGN PATENT DOCUMENTS

| | | |
|---|---|---|
| EP | 0 922 452 A1 | 6/1999 |
| EP | 0 922 456 A1 | 6/1999 |
| EP | 1 192 955 A2 | 4/2002 |
| EP | 1 014 938 B1 | 7/2002 |
| EP | 1 618 925 A1 | 1/2006 |
| EP | 1 992 367 A1 | 11/2008 |
| JP | 01-079108 A | 3/1989 |
| JP | 01-265019 A | 10/1989 |
| WO | WO 97/38735 A1 | 10/1997 |
| WO | WO 99/24551 A1 | 5/1999 |
| WO | WO 99/42131 A1 | 8/1999 |
| WO | WO 99/55303 A1 | 11/1999 |
| WO | WO 01/28339 A2 | 4/2001 |
| WO | WO 01/62224 A1 | 8/2001 |
| WO | WO 02/060502 A2 | 8/2002 |
| WO | WO 2005/044220 A1 | 5/2005 |
| WO | WO 2006/081071 A1 | 8/2006 |
| WO | WO 2007/144814 A1 | 12/2007 |
| WO | WO 2008/129494 A1 | 10/2008 |
| WO | WO 2009/125405 A2 | 10/2009 |

* cited by examiner

STABLE EMULSION FOR PREVENTION OF SKIN IRRITATION AND ARTICLES USING SAME

This application claims priority as a continuation of Application No. 61/666,407, filed on Jun. 29, 2012. The entirety of Application No. 61/666,407 is incorporated herein by reference.

BACKGROUND OF THE DISCLOSURE

The present disclosure relates generally to a formulation in the form of an emulsion which includes a combination of a gum blend and an electrolyte tolerant polymer, and items using same. The gum blend provides physical stability to an emulsion containing both clay and silicone oil. The emulsion of the present disclosure is useful for rash prevention and may be applied to the skin with a wipe wetted therewith or by other various means.

Wet wipes have been used for years for convenient skin cleansing between diaper changes. Much headway has been made in creating formulations for wet wipes. Such formulations are in the form of emulsions which provide a vehicle for the application of active ingredients to the skin. These ingredients may be used to treat and/or prevent diaper rash.

Diaper rash is a form of contact dermatitis which afflicts infants or incontinent persons whose wet and/or soiled absorbent garments are not promptly changed. Because of the practical impossibility of attending promptly to all of a person's needs, even those receiving a high level of care sometimes suffer from diaper rash. It has recently come to be understood that the initial stages of some types of diaper rash are the result of skin irritation caused by contact with digestive enzymes present in feces, particularly trypsin, chymotrypsin and elastase. These enzymes are proteolytic enzymes produced in the gastrointestinal tract to digest food. Similar conditions conducive to skin irritation by proteolytic enzymes present in feces are found in patients having colostomies. Such patients would also benefit from improved treatments to prevent skin irritation due to fecal enzymes.

Silicone oil is a commonly used active ingredient that acts as a skin barrier to prevent skin irritation. However, sometimes a skin barrier alone is not enough to prevent skin irritation, especially when fecal matter is present. Therefore, it is also desirable to sequester irritants such as proteolytic enzymes away from the skin.

Clay is one substance that can bind the protease enzymes found in fecal matter. Unfortunately, in all practicality, the benefits of clay and silicone oil cannot be realized in the same product due to physical instability. When clay and silicone oil are placed together into a highly aqueous emulsion, the emulsion tends to phase separate. Even without clay, an emulsion with a therapeutic amount (1% to 10% by weight) of silicone oil (e.g. dimethicone) can phase separate.

While there are several methods to achieve stable emulsions with silicone oil at concentrations compliant with its use as an over-the-counter drug, there are several disadvantages associated with these methods. First, the concentration of emulsifier required to successfully stabilize an emulsion containing the silicone oil, e.g. dimethicone, can be so great that it is cost prohibitive. Second, obtaining a low-viscosity, sprayable solution can be difficult due to the high probability that silicone oil droplets will coalesce, particularly at the elevated temperatures to which the solution may be exposed. Third, without appropriately modifying the rheology of the water phase, emulsions with a low viscosity and low solids content tend to undergo phase separation, particularly following a freeze-thaw cycle. This results in a non-uniform product that would not be efficacious.

Accordingly, there is a need for an emulsion that contains silicone oil as an active ingredient and does not phase separate even in the presence of clay. There is a further need to stabilize an emulsion containing silicone oil in a manner that is cost effective. It would be further advantageous if the formulation containing the emulsion and a sequestering solid such as clay would be suitable for spraying onto a substrate during the manufacture of a wet wipe. Additionally, there is a desire to apply preservatives to the emulsion, especially if it is to be applied to a natural substrate (e.g. cellulose) where there is more likelihood of microbe or fungal growth.

BRIEF DESCRIPTION OF THE DISCLOSURE

It has now been unexpectedly found that stable emulsions containing both silicone oil and clay can be formed with a gum blend. In particular, the gum blend contains one or more gums and propylene glycol alginate. One or more of the following gum(s) may be suitable: xanthan gum, guar gum, gellan gum, acacia gum, cellulose gum, dehydroxanthan gum, sclerotium gum and locust bean gum. The emulsion formed at about 95% water by weight is not only stable, but has a viscosity low enough to render it sprayable for the purpose of applying it to a wipe substrate.

Without being bound by theory, it is believed that propylene glycol alginate in combination with one or more gums provides an improved freeze-thaw stability by not only increasing the density of the water phase, but by imparting additional emulsification of the silicone oil. More specifically, large molecular-weight gums create a low viscosity network that bridges the silicate sheets (described herein) of the dissolved clay. Further, the gums are also salt tolerant as compared to typical rheology modifiers like acrylates, carbomer, polyquaternium-37, etc.

Accordingly, the present disclosure is directed to an oil-in-water emulsion including a glucoside-based emulsifier or a Gemini surfactant that is only present in the oil phase; a gum blend; a polymeric rheology modifier; 1% to 10% by weight silicone oil; 90% to 98% by weight water and a clay material in an effective mass amount to bind with the protease enzymes in a given amount of fecal mass. The gum blend contains at least one gum and propylene glycol alginate, wherein the gum blend is less than or equal to 0.5% by weight of the emulsion. The emulsion may be applied to a substrate to form a wet wipe.

Advantages due to the emulsion of the present disclosure include but are not limited to the following: cost effectiveness due to lower concentrations of emulsifier, the capability of being applied to a wipe substrate by spraying, and physical stability despite having both clay and silicone ingredients.

DETAILED DESCRIPTION OF THE DISCLOSURE

The present disclosure is directed to an emulsion for the prevention of skin irritation including among other ingredients, a stability enhancing system having a gum blend and an electrolyte tolerant polymer. The gum blend includes one more gums and propylene glycol alginate. Surprisingly, by employing the stability enhancing system of the present disclosure, the emulsion stays physically stable when both clay and dimethicone (about 1% to about 10% by weight) are combined in the emulsion.

Generally, the emulsion of the present disclosure contains a carrier medium, a barrier composition, an emulsifier system and a stability enhancing system. Additional ingredients, e.g. fragrance, botanicals, pH adjusting agents, buffers, preservatives, moisturizers and the like may be added to the emulsion.

Carrier Medium

Desirably, water serves as a medium for carrying the silicone oil and clay to the skin in an esthetically pleasing manner and at a suitable viscosity as discussed herein. In addition, water aids in the wetting of the substrate of the wipe product incorporating the emulsion. Typically, the emulsions of the present disclosure include from about 90% by weight to about 98% by weight water, including from about 92% by weight to about 97% by weight, and including from about 94% by weight to about 96% by weight.

Barrier Composition

The emulsions of the present disclosure include a barrier composition that serves to protect the skin from the digestive enzymes. Barrier composition components include silicone oil(s) and clay(s).

(a) Silicone Oil

The emulsions include silicone oil which is an active ingredient that functions primarily as a skin protectant against moisture (urine, sweat and overall humidity), and functions secondarily as an emollient. Desirable silicone oils are those that impart a tactile impression of softness and smoothness, and which do not impart an excessive tactile perception of greasiness, oiliness or coating when incorporated into the emulsion. Non-volatile silicone oils may be desirable over volatile silicone oils. Non-volatile silicone oils tend to remain stable when exposed to the environment, tend to provide a lasting tactile impression and tend to form a stable oil layer on the skin. Mixtures of silicone oils may be used. For example, volatile silicone oils may be combined with non-volatile silicone oils to impart desired esthetic properties as long as the emulsion contains sufficient non-volatile silicone to provide a skin barrier layer that is effective for a given application.

In one aspect, the silicone oil is dimethicone (linear polydimethylsiloxane). In this aspect of the disclosure, the emulsions of the present disclosure include from about 1% by weight to about 10% by weight dimethicone, including from about 1% by weight to about 5% by weight, and including from about 1% by weight to about 3% by weight. Other exemplary silicone oils that are suitable for use herein include dimethiconol, ethoxylated dimethicone (linear and pendant varieties), amodimethicone and derivatives thereof, cyclomethicone, alkyl substituted derivatives such as stearyl dimethicone and behenyl dimethicone, phenyl trimethicone and mixtures thereof. Such silicones are commercially available, for example, from the Dow Corning Company of Midland, Mich. under the names XIAMETER PMX-200 Silicone Fluid (Dimethicone), XIAMETER PMX-1184 Silicone Fluid (Trisiloxane and Dimethicone), DOW CORNING 1403 Fluid (Dimethicone and Dimethiconol), DOW CORNING 1501 Fluid (Cyclopentasiloxane and Dimethiconol), DOW CORNING 593 Fluid (Dimethicone and Trimethylsiloxysilicate), DOW CORNING 2502 Fluid (Cetyl Dimethicone), and DOW CORNING 558 Fluid (Phenyl Trimethicone).

(b) Clay

In a traditional emulsion, oil droplets are solubilized by an emulsifier system. The viscosity of the traditional emulsion arises from the relatively high concentration of oil droplets, and the use of a rheology/viscosity agent to provide a sufficient resistance to flow at all shear rates. The rheology/viscosity agent prevents small emulsion oil droplets from forming larger, more unstable droplets that eventually result in complete separation of the oil phase, sometimes called Ostwald ripening.

The present disclosure utilizes the combination of clays to provide a significant yield (resistance to flow) without the concomitant increase in viscosity across all shear rates along with an emulsifying system that is capable of stabilizing relatively low levels of silicone oil in small droplets. Through the use of clays and emulsifying systems described herein one can achieve a low viscosity and stable emulsion suitable for spraying.

Suitable clays include natural smectite clays that have been water washed. One such clay is magnesium aluminum silicate, available from R.T. Vanderbilt Company, Inc. under the VEEGUM ULTRA brand. Additional commercial products for clays include Veegum PRO, Gel White H, Gelwhite GP, Gelwhite H also from R.T. Vanderbilt Company and Mineral Colloid BP from Southern Clay. Characteristics of smectite clays include the ability to swell in water to impart desirable rheological properties to aqueous compositions.

Smectite clays have a colloidal structure in water. Each smectite particle can be thought of as a collection of submicroscopic platelets, each platelet having a negative charge at the face thereof, and positive charge at the edge. When hydrated, the cations diffuse away from the platelets, promoting delamination of same. The speed at which platelet separation occurs is directly related to the amount of energy introduced during hydration, both mechanical and thermal. High-shear mixing and warm water reduce hydration time.

Smectite dispersions are thixotropic and pseudoplastic. In addition, they have the ability to impart at low viscosity a certain minimum force known as a "yield value". The yield value relates to the measure of resistance of the colloidal structure to breakdown. A force equal to the yield value is applied to start disruption of the colloidal structure. A force greater than the yield value is applied to enable movement through the emulsion. The greater the yield value, the more stable the emulsion.

Another desirable characteristic is that when mixed with salts and surfactants, the smectite viscosity and yield value will increase, and the thixotropy will decrease. However, the smectite will still provide a shear-thinning emulsion.

Smectite eliminates the tacky, gummy or stringy nature of organic gums and polymers. There is a synergistic effect between smectite clay and the organic gums/polymers. The smectite contributes to viscosity and yield value, while the gums/polymers collioidal action improves the clay stability in the presence of electrolytes, surfactants and other water soluble ingredients.

A desirable amount of clay is an amount that binds a desirable portion of the protease enzymes in a given sample of proteolytic digestive enzymes using the Test Method to Determine Binding of Fecal Protease. To "bind" means that the proteolytic enzymes possess an overall positive charge and are attracted/physisorbed to the anionic clay platelets through an electrostatic interaction. In one aspect an "effective amount" of clay maybe defined as an amount of clay in a formulation such that when a pre-determined amount of formulation is thoroughly mixed with a pre-determined amount of protease enzyme solution, the clay binds to at least about 50% of the protease enzymes present in the solution. Desirably, the amount of smectite clay in the emulsion is between about 0.1% to about 3% by weight of the emulsion.

Emulsifier System

In addition to the carrier and the barrier composition, the emulsions of the present disclosure include an emulsifier system for forming oil-in-water emulsions. The emulsifier system is a synergistic combination of specific ingredients which emulsify other formulation components that would not otherwise mix together in a stable manner. It is capable of de-emulsifying upon application of the complete formulation to the skin thereby forming a silicone oil film on the skin. The emulsifier system does not tend to re-emulsify once the emulsion is applied to the skin and exposed to urine or other body fluids. This prevents the silicone oil from being washed away by urine.

Specifically, the emulsifier system includes two components: (a) either a Gemini surfactant only present in the oil phase, a glucoside-based emulsifier or a combination thereof.

(a) Gemini Surfactant

Gemini surfactants are a special class of surfactants that contain multiple hydrophobic tails and multiple hydrophilic head groups within the same molecule. Gemini surfactants can be ten to a thousand times more surface active than conventional surfactants with similar but singular hydrophilic and hydrophobic groups in the molecule. Gemini surfactants may reduce skin irritation in addition to serving as an emulsifier.

Gemini surfactants are believed to form liquid crystalline lamellar gel networks in the oil phase which result in the formation of very small oil droplets. The small size and gel-like nature of the droplets provides resistance against coalescence of the droplets eventuating in complete oil phase separation. In addition, Gemini surfactants have been shown to not have the HLB dependency for oil emulsification of typical ethoxylated fatty alcohols, ethoxylated fatty esters, and other common non-Gemini surfactant emulsifiers.

Many Gemini surfactants were explored in an effort to create a stable emulsion containing dimethicone and clay, and surprisingly, most did not work. One Gemini surfactant that was found to work in an emulsion having 95.15% water was Disodium Ethylene Dicocamide PEG-15 Disulfate. In one aspect of the disclosure, this Gemini surfactant is blended with Behenyl Alcohol (and) Glyceryl Stearate (and) Glyceryl Stearate Citrate, and is available from Sasol North America, Inc. as CERALUTION H.

(b) Glucoside-Based Emulsifier

A glucoside-based emulsifier (referred to as a glucoside emulsifier) may be used in lieu of or in addition to the Gemini surfactant. Other non-ionic surfactants, tested alone or in combination with other such surfactants, that failed to perform satisfactorily include: Glyceryl Stearate, PEG-100 Stearate, Sorbitan Sesquioleate, Undeceth-3, Undeceth-8, PEG-20 Methyl Glucose Sesquistearate, Tridececeth-3, Tridedeceth-12, Laureth-9, Behenoyl Stearic Acid, Oleth-2, Oleth-20, Cetearyl Olivate, Sorbitan Olivate, Polawax A-31, Sorbitan Laurate, Sorbitan Palmitate, Sorbitan Oleate, Steric Acid, Sorbitan Trioleate, Steareth-2, Steareth-20, Steareth-21, Laureth-23, Laureth-2, C11-15 Pareth-15, PPG-24-Buteth-27, Glyceryl Stearate Citrate, PEG/PPG-20/6 Dimethicone, Bis-PEG/PPG-20/20 Dimethicone, Bis-PEG/PPG-16/16 PEG/PPG-16/16 Dimethicone, Bis-PEG/PPG-20/5 PEG/PPG-20/5 Dimethicone, Methoxy PEG/PPG-25/4 Dimethicone, Bis-PEG/PPG-14/14 Dimethicone, PEG-11 Methyl Ether Dimethicone, PEG/PPG-20/22 Butyl Ether Dimethicone, Lauryl PEG-9 Polydimethylsiloxyethyl Dimethicone, PEG-10 Dimethicone, Polyglyceryl-3 Disiloxane Dimethicone, Lauryl Polyglyceryl-3 Polydimethylsiloxyethyl Dimethicone, Cetyl PEG/PPG-10/1 Dimethicone, Polyglyceryl-4 Isostearate, Cetyl PEG/PPG-10/1 Dimethicone, Lauryl PEG-8 Dimethicone, Sucrose Laurate, Sucrose Myristate, Sucrose Stearate, Polyglyceryl-10 Decaoleate, Polyglyceryl-4 Laurate, Diisostearoyl Polyglyceryl-3 Dimer Dilinoleate, Polyglyceryl-2 Sesquiisostearate. In addition, anionic and cationic surfactants failed to perform satisfactorily as well. Glucoside emulsifiers are generally formed by the condensation of glucose with varied fatty alcohols. More specifically, the glucoside emulsifiers are combined with a fatty alcohol, such as cetearyl alcohol, to create stable emulsions. Glucoside emulsifiers are known to promote liquid crystals around oil droplets in the continuous phase, thereby enhancing distribution on skin of the barrier forming materials such as dimethicone. Specific glucoside based emulsifiers that are commercially available include but are not limited to MONTANOV 202, MONTANOV 68, MONTANOV 82, MONTANOV S, MONTANOV L, SEPISOFT 20-22, available from Seppic, Paris, France; and POLY SUGAPHOS 1000P, POLY SUGANATE 100P, SUGANATE 100 AND SUGANATE 160 available from Colonial Chemical, Inc, South Pittsburg, Tenn.

Stability Enhancing System

The stability enhancing system is defined by one or more gums and an electrolyte tolerant polymer.

a) Gum Blend

The gum blend may be a single gum or multiple gums. One desirable gum blend includes xanthan gum and/or guar gum. In certain applications, it may be advantageous to substitute the xanthan gum and/or guar gum with one or more of the following: gellan gum, acacia gum, cellulose gum, dehydroxanthan gum, sclerotium gum and locust bean gum. The gum blend further includes propylene glycol alginate. Without being bound by theory, it is believed that propylene glycol alginate serves to improve freeze-thaw stability by not only increasing the density of the water phase, but by imparting additional emulsification of the silicone oil.

Like clay and acryloyldimethyl taurate polymers, gums are rheological modifiers which are used in conjunction with the propylene glycol alginate. Other classes of rheological modifiers such as starches may be used in combination with propylene glycol alginate provided that a stable emulsion is achieved using less than 0.5% by weight rheological modifiers and the viscosity of the formulation measures below 5,000 centipoise.

Desirably, the gum blend is used in an amount between about 0.01 to about 0.5% by weight of the emulsion.

b) Electrolyte Tolerant Polymer

The emulsions of the present disclosure further include an electrolyte-tolerant polymeric serving as a rheology modifier to provide additional structure to the formulation and to prevent the oil droplets from coalescing.

Without being bound by theory, it is believed that electrolyte-tolerant polymers provide an increase in viscosity to the complete formulation without interfering with the clay, despite the presence of ionic species. With typical acrylate-based rheology modifiers, the addition of clays and ionic surfactants results in the collapse of the polymer thereby removing all rheology imparted by the polymer. It has been found that certain classes of polymeric rheology modifiers can survive the ionic strength of formulations of the present disclosure and retain their rheological profile. Examples of electrolyte-tolerant polymeric rheology modifiers include those utilizing the acryloyldimethyl taurate monomers, such as GRANSIL APK-1 available from Grant Industries, Inc., Elmwood Park, N.J.; and SEPINOV EMT 10, SEPIPLUS S, SIMULGEL FL, SIMULGEL EG, SIMULGEL 800, AND SIMULGEL NS, all available from Seppic, Paris, France. Typically, the emulsions of the present disclosure include from about 1% by weight to about 30% by weight of an electrolyte-tolerant polymeric rheology modifier utilizing an acryloyldimethyl taurate monomer, including from about 0.05% to about 0.50% by weight of the material as supplied, and including from about 0.1% to about 0.25% by weight.

Optional Ingredients (a) pH Adjusting Agent

The emulsions of the present disclosure may further include a pH-adjusting agent. Such agents are desirable for the creation of emulsions having a pH at or near that of human skin. Therefore, the pH will typically be adjusted as necessary so that the emulsion of the present disclosure has a pH of from 4 to 7, or more desirably, from 4.5 to 6.5. The pH can be adjusted by adding one or more pH-adjusting agents in an amount effective to provide such pH values ("effective amount"). Agents that may be used to adjust the pH of the emulsions include organic and inorganic acids and bases.

For the more desirable emulsions of the present disclosure, the emulsion (in the absence of a pH-adjusting agent) tends to be more basic than desired. Therefore, an acid pH-adjusting agent will typically be used to bring the emulsion to the desired pH. Acid pH-adjusting agents include organic acids which are relatively non-irritating. Such acids include malic acid, citric acid acetic acid, propionic acid, oxalic acid, glycolic acid, malonic acid, lactic acid, succinic acid, tartaric acid, aspartic acid, maleic acid, glutaric acid, glutamic acid, gluconic acid, sorbic acid, benzoic acid, ascorbic acid, salicylic acid and mixtures thereof. In one aspect of the present disclosure, a desirable pH-adjusting agent is malic acid.

The amount of the pH-adjusting agent that is employed depends on the equivalent weight of the pH-adjusting agent and the desired pH. Typically, the pH-adjusting agent is used in an amount of from about 0.05% to about 0.5% by weight of the emulsion. Desirable emulsions of the present disclosure include from about 0.1% to about 0.5% percent, and typically about 0.2% to about 0.3% percent of the pH-adjusting agent.

(b) Preservatives

Preservatives function in one or more ways to improve the shelf life of the emulsions and products incorporating same. For example, the preservative may be an anti-microbial agent, an anti-bacterial agent, an anti-fungal agent, or a combination thereof.

Preservatives herein include, but are not limited to, benzethonium chloride, benzisothiazolinone, benzoic acid, benzyl alcohol, 2-Bromo-2-nitropropane-1,3-diol, butylparaben, caprylyl glycol, chlorhexidine digluconate, DMDM hydantoin, diazolidinyl urea, dehydroacetic acid, ethylparaben, iodopropynyl butylcarbamate, methylchloroisothiazolinone, methylisothiazolinone, methyldibromo glutaronitrile, methylparaben, pentylene glycol, phenethyl alcohol, phenoxyethanol, propylparaben, polyaminopropyl biguanide, quaternium-15, salicylic acid, sodium benzoate, sodium methylparaben, sodium dehydroacetate, thymol, triclosan and mixtures thereof.

In one aspect of the disclosure, benzoic acid, with or without phenoxyethanol, is effective in preventing the growth of a wide variety of microbes and fungi. Such protection tends to be particularly desirable where the wipe product contains a porous substrate, for example, nonwoven substrates.

Desirably, wet wipes have a shelf life of at least two years under storage conditions of about 75 degrees Fahrenheit and 50 percent relative humidity. Certain agents may be employed to achieve the desired term, one of which is an anti-microbial agent. The anti-microbial agent may be used in an amount that is effective to provide the desired shelf life (storage stability, i.e., microorganisms do not grow to a significant extent) (herein alternatively referred to as "an effective amount"). This includes demonstrating sufficient anti-microbial activity in accordance with United States Pharmacopeia test entitled "Microbial Test, Antimicrobial Preservative—Effectiveness".

(c) Chelating Agent

The emulsion may contain one or more chelating agents. The chelating agent tends to bind metals (e.g., calcium ions, magnesium ions) that may be present in the emulsion so as to enhance the efficiency of the emulsifier and the anti-microbial agent. Thus, the chelating agent may be considered to provide a level of anti-microbial activity to function as a preservative. The chelating agent may be used in an amount that is effective to bind the aforementioned metals (hereinafter alternatively referred to as an "effective amount"), typically an amount ranging from about 0.01 percent to about 0.2 weight percent of the emulsion. Particularly preferred emulsions include from about 0.05% to about 0.2% by weight, more preferably from about 0.05% to about 0.10% by weight. Chelating agents and their use in personal cleansing emulsions are well known in the art. Exemplary chelating agents include disodium EDTA, trisodium EDTA, tetrasodium EDTA, and tetrasodium iminodisuccinate.

(d) Other

The emulsion of the present disclosure may optionally include other ingredients, e.g., fragrance; skin soothing aids such as aloe, lavender, chamomile, green tea, calendula, etc.; skin moisturizers (humectants) such as glycerin, propylene glycol, betaine, and hydroxyethyl urea; or emollients other than those previously described; powders and the like.

Viscosity

While the examples herein show a highly aqueous emulsion, it is noted that emulsions with lower levels of water and thus higher viscosities may be desired, especially when applied to the skin by means other than a wet wipe. For instance, the emulsion may be formulated to be a lotion, gel or paste. However, for application to wipe substrates as disclosed herein, it is desirable to have a viscosity at 25 degrees Celsius of about 5000 centipoise (cps) or less, or in other applications, 4000 cps or less as obtained using a Brookfield DV-II Viscometer with spindle 5 at 6 r.p.m.

EXAMPLES

TABLE 1 shows seven highly aqueous, stable dimethicone emulsions with a viscosity less than 5,000 cps. They are denoted as base formulations F1-F7. These seven examples are deemed stable using the Freeze-Thaw Test Method disclosed herein.

TABLE 2 demonstrates the compatibility of various clays for emulsions without the gum blend of the present disclosure. A positive compatibility is achieved when the formulation does not separate at room temperature overnight.

TABLE 3 demonstrates three rash-preventative emulsions containing clay and dimethicone, with a viscosity less than 5,000 cps. Each formulation was deemed stable using Freeze-Thaw Test Method.

TABLE 4 demonstrates the percentage of protease recovered from formulations with the additive Magnesium Aluminum Silicate (VEEGUM ULTRA) (F8, F9, F10) versus without this additive (F8', F9', F10').

TABLE 1

| Trade Name | INCI Name | % wt F1 | % wt F2 | % wt F3 | % wt F4 | % wt F5 | % wt F6 | % wt F7 |
|---|---|---|---|---|---|---|---|---|
| Part A+ | | | | | | | | |
| Water | Water | 95.15 | 95.15 | 95.15 | 95.15 | 95.15 | 95.15 | 94.15 |
| ARAGUM 3173 | Xanthan Gum (and) Guar Gum (and) Propylene Glycol Alginate | 0.50 | 0.50 | 0.50 | 0.50 | 0.50 | 0.50 | 0.50 |
| Part B | | | | | | | | |
| CETIOL 868 | Ethylhexyl Stearate | 0.50 | 0.50 | 0.50 | 0.50 | 0.50 | 0.50 | 0.50 |
| CETIOL SN | Cetearyl Isononanoate | 0.50 | 0.50 | 0.50 | 0.50 | 0.50 | 0.50 | 0.50 |
| DC 200, 100 CST | Dimethicone | 1.50 | 1.50 | 1.50 | 1.50 | 1.50 | 1.50 | 1.50 |
| MONTANOV 68 | Cetearyl Alcohol (and) Cetearyl Glucoside | 1.00 | — | — | — | — | — | — |
| MONTANOV 82 | Cetearyl Alcohol (and) Coco-Glucoside | — | 1.00 | — | — | — | — | — |
| PROLIPID 151 | Stearic Acid (and) Behenyl Alcohol (and) Glyceryl Stearate (and) Stearyl Alcohol (and) Cetyl Alcohol (and) Palmitic Acid (and) Hydroxyethyl Cetearamidopropyldimonium Chloride (and) Myristyl Alcohol | — | — | 1.00 | — | — | — | — |
| MONTANOV L | C14-22 Alcohols (and) C12-20 Alkyl Glucoside | — | — | — | 1.00 | — | — | — |
| CRODAFOS CS20A | Cetearyl Alcohol and Ceteth-10 Phosphate and Cetyl Diphosphate | — | — | — | — | 1.00 | — | — |
| MONTANOV S | Coco-Glucoside (and) Coconut Alcohol | — | — | — | — | — | 1.00 | — |
| CERALUTION H | Behenyl Alcohol (and) Glyceryl Stearate(and) Glyceryl Stearate Citrate (and) Disodium Ethylene Dicocamide PEG-15 Disulfate | — | — | — | — | — | — | 2.00 |
| Part C | | | | | | | | |
| PUROX S | Sodium Benzoate | 0.45 | 0.45 | 0.45 | 0.45 | 0.45 | 0.45 | 0.45 |
| BRONIDOX 1160 | Phenoxyethanol | 0.40 | 0.40 | 0.40 | 0.40 | 0.40 | 0.40 | 0.40 |

+Parts A and B refer to ingredients in the oil and water phases respectively, and Part C is ingredients added to the formulation upon formation of the emulsion.

TABLE 2

| | | Base Formulation | | | | | | |
|---|---|---|---|---|---|---|---|---|
| Clay Trade Name | INCI Name | F1 | F2 | F3 | F4 | F5 | F6 | F7 |
| MINERAL COLLOID BP | Bentonite | No | Yes | No | No | No | Yes | Yes |
| VEEGUM PRO | Tromethamine Magnesium Aluminum Silicate | No | Yes | No | No | No | No | Yes |
| VEEGUM Ultra | Magnesium Aluminum Silicate | No | Yes | No | Yes | Yes | No | Yes |
| LAPONITE XLG | Sodium Aluminum Silicate | No | Yes | No | No | No | No | Yes |
| GELWHITE GP | Montmorillonite | No | Yes | No | Yes | No | Yes | Yes |

TABLE 3

| Trade Name | INCI Name | F8 % wt | F9 % wt | F10 % wt |
|---|---|---|---|---|
| Part A | | | | |
| Water | Water | 95.15 | 95.15 | 95.15 |
| VEEGUM ULTRA | Magnesium Aluminum Silicate | 0.50 | 0.50 | 0.50 |
| ARAGUM 3173 | Xanthan Gum (and) Guar Gum (and) Propylene Glycol Alginate | 0.50 | 0.25 | 0.50 |
| Part B | | | | |
| CETIOL 868 | Ethylhexyl Stearate | 1.00 | 1.00 | 1.00 |
| DC 200, 100 CST | Dimethicone | 1.50 | 1.50 | 1.50 |
| MONTANOV 82 | Cetearyl Alcohol (and) Coco-Glucoside | 0.50 | 0.50 | — |
| CERALUTION H | Behenyl Alcohol (and) Glyceryl Stearate (and) Glyceryl Stearate Citrate (and) Disodium Ethylene Dicocamide PEG-15 Disulfate | — | — | 0.50 |
| Steric Acid | Steric Acid | 0.25 | — | — |
| SEPINOV EMT10 | Hydroxyethyl Acrylate/Sodium Acryloyldimethyl Taurate Copolymer | 0.25 | — | — |
| ARISTOFLEX | Ammonium | — | 0.25 | 0.25 |

TABLE 3-continued

| Trade Name | INCI Name | F8 % wt | F9 % wt | F10 % wt |
|---|---|---|---|---|
| AVC | Acryloyldimethyltaurate/VP Copolymer | | | |
| Part C | | | | |
| PUROX S | Sodium Benzoate | 0.45 | 0.45 | 0.45 |
| BRONIDOX 1160 | Phenoxyethanol | 0.40 | 0.40 | 0.40 |
| Malic Acid (30% Solution) | Malic Acid | 0.30 | 0.30 | 0.30 |

Parts A and B refer to ingredients in the oil and water phases respectively, and Part C is ingredients added to the formulation upon formation of the emulsion.

TABLE 4

| Base Formulation Number | Percent Clay in Formula | Percent of Recovered Protease | Percent Protease Bound |
|---|---|---|---|
| F8 | 0.5 | 37.3 | 62.7 |
| F8' | 0.0 | 100.0 | 0.0 |
| F9 | 0.5 | 11.1 | 88.9 |
| F9' | 0.0 | 100.0 | 0.0 |
| F10 | 0.5 | 32.0 | 68.0 |
| F10' | 0.0 | 100.0 | 0.0 |

TABLE A

| | 1 | 2 | 3 | 4 | 5 | 6 | 7 | 8 | 9 | 10 | 11 | 12 |
|---|---|---|---|---|---|---|---|---|---|---|---|---|
| A | 200 uL protease sol'n (std curve) | 200 uL lotion 1 | 200 uL lotion 2 | 200 uL lotion 3 | 200 uL lotion 4 | 200 uL lotion 5 | 200 uL lotion 6 | 200 uL lotion 7 | 200 uL lotion 8 | 200 uL lotion 9 | 200 uL Protease Buffer | |
| B | | | | Pipette 100 ul 100 mM Tris (pH 8) to well in rows B-H | | | | | | | | |
| C | | | | | | | | | | | | |
| D | | | | Serially dilute 100 ul down plate to row G | | | | | | | | |
| E | | | | | | | | | | | | |
| F | | | | discard 100 ul from row H | | | | | | | | |
| G | | | | | | | | | | | | |
| H | | | | Add 100 ul 5 mM BAPNA in water to all wells; immediately read plate | | | | | | | | |
| A | 100 | ug/ml enzyme = | 50 | | ug/ml after adding BAPNA = | | 20 | ug/well | | | 0 | |
| B | 50 | | 25 | | | | 10 | | | | | |
| C | 25 | | 12.5 | | | | 5 | | | | | |
| D | 12.5 | | 6.25 | | | | 2.5 | | | | | |
| E | 6.25 | | 3.125 | | | | 1.25 | | | | | |
| F | 3.125 | | 1.5625 | | | | 0.625 | | | | | |
| G | 1.5625 | | 0.78125 | | | | 0.3125 | | | | | |
| H | 0 | | 0 | | | | 0 | | | | | |

A score of 100 indicates that none of the fecal protease was bound by the formulation. Thus, emulsions without magnesium aluminum silicate (F8', F9' and F10') are not suitable for binding fecal protease.

A desirable level of gum blend is one that creates of emulsion stability, maintains a low viscosity and effectively binds clay to the fecal proteases responsible for skin irritation. The amount of gum blend suitable for maintaining emulsion stability is dependent on the clay effectiveness in binding fecal proteases and the relative proportion of the gum blend components.

Wipe Substrates and Emulsion Add-On Levels

As used herein, the term "substrate" means any material suitable for carrying the emulsion of the present disclosure. Suitable substrates include any material that does not hinder the clay's affinity for binding skin irritants or the deposition of emulsion components onto the skin, and that do not cause skin irritation. Substrates may be water dispersible.

Examples of suitable substrates include, but are not limited to, woven or non-woven webs, spunbond fabric, meltblown fabric, knit fabric, wet-laid fabric, scrims, needle-punched webs, synthetic fibers and natural fibers. It is to be understood that these suitable substrates are not mutually exclusive and can be used in a combination.

The choice of substrate fibers depends upon, for example, fiber cost and the desired properties. For example suitable fibrous materials may include, but are not limited to, synthetic fibers such as those derived from polyolefins, polyesters, polyamides, polyacrylics, polyethylene, polypropylene, polyvinyl, etc., alone or in combination with one another. Similarly, natural fibers such as cotton, linen, hemp, jute, wool, wood pulp, etc.; regenerated cellulosic fibers such as viscose rayon and cuprammonium rayon or modified cellulosic fibers, such as cellulose acetate may likewise be used. Blends of one or more of the above fibers may also be used if so desired.

As used herein, the term "nonwoven fabric" refers to a fabric having a structure of individual fibers or filaments which are randomly and/or unidirectionally interlaid in a mat-like fashion. Nonwoven fabrics can be made from a variety of processes including, but not limited to, air-laid processes, wet-laid processes, hydroentangling processes, staple fiber carding and bonding, and solution spinning. Suitable nonwoven fabrics include, but are not limited to, spunbond fabrics, meltblown fabrics, wet-laid fabrics and combinations thereof.

As used herein, the term "spunbond fabric" refers to a web of small diameter fibers and/or filaments which are formed by extruding a molten thermoplastic material, or coextruding more than one molten thermoplastic material, as filaments from a plurality of fine, usually circular, capillaries in a spinnerette with the diameter of the extruded filaments then being rapidly reduced, for example, by non-eductive or eductive fluid-drawing or other well-known spunbonding mechanisms. The production of spunbond nonwoven webs is well-known and illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Petersen, U.S. Pat. No. 3,502,538; Hartman, U.S. Pat. No. 3,502,763; Dobo et al., U.S. Pat. No. 3,542,615; and Harmon, Canadian Pat. No. 803,714.

As used herein, the term "meltblown fabrics" refers to a fabric comprising fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers. The meltblown process is well-known and is described in various patents such as U.S. Pat. No. 3,849,241 to Butin, et al.

As used herein, the term "microfibers" means small diameter fibers having an average diameter not greater than about 100 microns, for example, having a diameter of from about 0.5 microns to about 50 microns. More specifically microfibers may also have an average diameter of from about 1 micron to about 20 microns. Microfibers having an average diameter of about 3 microns or less are commonly referred to as ultra-fine microfibers.

As used herein, the term "wet-laid fabrics" refers to fabrics formed by a process, such as a paper-making process, wherein fibers dispersed in a liquid medium are deposited onto a screen such that the liquid medium flows through the screen, leaving a fabric on the surface of the screen. Fiber bonding agents may be applied to the fibers in the liquid medium or after being deposited onto the screen. Wet-laid fabrics may contain natural and/or synthetic fibers.

As used herein, the term "spunlace fabrics" refers to a web of material consisting of a blend of natural fibers and synthetic fibers, where the fibers are subjected to high-velocity water jets which entangle the fibers to achieve mechanical bonding. Desirably, the natural fibers are wood pulp fibers and the synthetic fibers are polyester fibers.

As used herein, the terms "needle-punched" and "needled" refer to a web of material consisting of one or more fibrous materials, wherein the fibers are subjected to needles which entangle the fibers to achieve mechanical interlocking without the need for adhesives or chemical additives.

As used herein, the term "woven fabric" refers to a fabric containing a structure of fibers, filaments or yarns, which are orderly arranged in an interengaged fashion. Woven fabrics typically contain interengaged fibers in a "warp" and "fill" direction. The warp direction corresponds to the length of the fabric while the fill direction corresponds to the width of the fabric. Woven fabrics can be made on a variety of looms including, but not limited to, shuttle looms, Rapier looms, projectile looms, air jet looms and water jet looms.

The composition of the present disclosure formulation may be incorporated into the basesheet in an add-on amount of from about 50% (by weight of the basesheet) to about 800% (by weight of the basesheet). More specifically, the formulations may be incorporated into the basesheet in an add-on amount of from about 200% (by weight of the basesheet) to about 600% (by weight of the basesheet) or from about 400% (by weight of the basesheet) to about 600% (by weight of the basesheet). The formulation add-on amounts may vary depending on the composition of the basesheet.

Experimental Methods (a) Method of Making Test Formulations

Generally, the procedure used to make the emulsions used for testing includes the following steps:
1. If clays such as Bentonite clay or Magnesium Aluminum Silicate are added to the water phase of the formulation, hydrate them according to manufacturer's recommendations for time, temperature and shear. Once hydrated, using rapid mixing, add the clay to a beaker containing purified water.
2. Heat the water phase of the formulation to 75 degrees Celsius while slowly adding the gum blend.
3. Combine materials of the oil phase of the formulation and heat them to 75 degrees Celsius under conditions of constant mixing.
4. Add the oil phase to the water phase and homogenize the mixture at 5000 to 7000 rpm for five minutes using a SILVERSON homogenizer available from Silverson Machines, Inc.
5. Cool the mixture to 35 degrees Celsius under conditions of constant mixing.
6. Add preservatives if desired.
7. Adjust pH to 4.5+/−0.5 using an acid.
8. Homogenize the mixture again for two minutes at 2000 to 3000 rpm.

(b) Test to Determine Binding of Fecal Protease

The following method is used to measure the fecal binding property.

Materials:
1. Frozen Trypsin/chymotrypsin from Specialty Enzymes and Biochemicals Co., Chino, Calif. (lot#106161), 1 mg=2695 USP trypsin and 274 USP chymotrypsin
2. 1×PBS pH 7.4 from GIBCO, item #10010
3. $N_\alpha$-Benzoyl-DL-arginine 4-nitroanilide hydrochloride (BAPNA) from Sigma-Aldrich Corporation ("Sigma"), item #B4875
4. Dimethylsulfoxide (DMSO) from Sigma, item #D8418
5. Tris-HCl, 1M, from Sigma, item #T2694
6. Sodium Acetate (NaOAc) from Sigma
7. Sodium Chloride (NaCl) from Sigma
8. 96 well microtiter plates, clear, Nunc brand from Thermo Fisher Scientific, Inc.
9. 1.7 mL microcentrifuge tubes from VWR International, LLC
10. COSTAR® SPIN-X® centrifuge tube filter (0.22 mm cellulose acetate) in a 2.0 mL microcentrifuge tube from Corning Inc., item #8161
11. Reagent reservoirs from VWR International, LLC
12. EPPENDORF® pipettors from Cole-Parmer, 100, 200 and 1000 µL volumes
13. Sterile EPPENDORF® tips from Cole-Parmer for pipettes in #12

Methods:
1. Protease Buffer
   1.1. 50 mM NaOAc (prepared and kept refrigerated)
   1.2. 0.15M NaCl (7.012 g added to 800 mL of NaOAc)
   1.3. Keep refrigerated
2. Stock Protease solution
   2.1. Prepare frozen protease stock and freeze for future use (5 mg/mL)
      2.1.1. 0.5 g protease into 100 mL Protease buffer
      2.1.2. Aliquot into 2 mL microcentrifuge tubes
      2.1.3. Freeze in −20° C. freezer
3. Working Protease Buffer
   3.1. 24.5 mL of chilled Protease Buffer
   3.2. 500 µL of thawed stock protease solution
   3.3. Hold in ice bucket
4. Lotion Preparation—10% lotion blend
   4.1. 100 µL lotion—use positive displacement pipette
   4.2. 900 µL working protease buffer
   4.3. Place into 2.0 ml microcentrifuge tube
   4.4. Mix by inversion; flick end of tube to mix lotion
5. Protease Controls
   5.1. 1000 µL working protease buffer
6. Place samples and control onto THERMOLYNE VARI-MIX and rock 20 minutes to uniformly mix
7. Remove 100 µL into 2.0 mL SPINX tube; centrifuge 5 minutes at 4,000 rpm 8. Prepare microtiter plate (see below) for Enzyme Activity Assay
9. Reagent Preparation
    9.1. Prepare 5 mM BAPNA working solution from 50 mM stock
        9.1.1. BAPNA Stock (50 mM in DMSO) (may be frozen)
            9.1.1.1. Weigh 0.217 g BAPNA into 10 mL DMSO
            9.1.1.2. Working BAPNA Solution (dilute 1:10 for 5 mM solution)
                9.1.1.2.1. Pipette 9 ml water into 15 ml centrifuge tube
                9.1.1.2.2. Pipette 1.0 mL 50 mM Stock BAPNA into tube
                9.1.1.2.3. Mix and hold at room temp until use that same day
    9.2. Prepare 100 mM Tris, pH 8
        9.2.1. Dilute 1M Tris pH 8 1:10
            9.2.1.1. Measure 90 mL laboratory Milli-Q water into bottle
            9.2.1.2. Pipette 10 mL 1M Tris into bottle
            9.2.1.3. Mix, measure pH
10. Enzyme Activity Assay—
    10.1. Set-up plate reader
        10.1.1. Turn on SPECTRAMAX PLUS 364 Molecular Devices plate reader
        10.1.2. Protocol:
            10.1.2.1. Kinetic Read at 405 nm
            10.1.2.2. Read every 20 seconds for 10 minutes
            10.1.2.3. Disregard readings from first 2 minutes
            10.1.2.4. Plate Set-up
                10.1.2.4.1. Columns 1-2: 200 µl standard
                10.1.2.4.2. Rows A-D are 500 µg/ml protease/bile acid cocktail
                10.1.2.4.3. Rows E-H are 100 µg/ml protease/bile acid cocktail
                10.1.2.4.4. Column 12 contains blanks
                10.1.2.4.5. Series dilutions across plate, left to right
                10.1.2.4.6. Starting concentration is 20 µg/ml with 2 fold dilutions
    10.2. Set-up the microtiter plate as shown in TABLE A.
        10.2.1. Pipette 100 µL 100 mM Tris into all wells of 96 microtiter plate except row A
        10.2.2. Add 200 µL of controls to A1 and A2
        10.2.3. Add 200 µl of lotion preps according to the above picture
        10.2.4. Remove 100 µL from row A into row B
        10.2.5. Mix contents of row B by slowly aspirating and re-pipetting contents 4 times
        10.2.6. Continue down the plate removing 100 µL from one row into the next with mixing until reaching row G
        10.2.7. After mixing remove and discard 100 µL from row G
        10.2.8. Add 100 µL 5 mM Working BAPNA Solution to all wells
        10.2.9. Immediately read the plate for 10 minutes
    10.3. Calculate mOD/min.
        10.3.1. Within the software review the plots
        10.3.2. Adjust the assay time to use data from 2-5 minutes (120-300 seconds)
        10.3.3. Plot the mOD/min for the wells exhibiting good straight line ($r^2$=0.98 or better) versus the µg/well.

(c) Stability Test

The purpose of this test is to demonstrate formulation stability upon exposure to possible freezing during shipping or storage. The test is performed by freezing the composition at minus 20 degrees Celsius. Once frozen, the composition is allowed to completely thaw at room temperature. This freeze-thaw cycle is conducted for a total of three times. The test results are determined by visual inspection for phase separation.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above formulations without departing from the scope of the disclosure, it is intended that all matter contained in the above description shall be interpreted as illustrative and not in a limiting sense.

The invention claimed is:

1. An emulsion for the prevention of skin irritation, the emulsion comprising:
    a Gemini surfactant present only in the oil phase or a glucoside-based emulsifier;
    a combination of a gum and propylene glycol alginate, wherein the combination is 0.01% to 0.5% by weight of the emulsion;
    a polymeric rheology modifier comprising an acryloyldimethyl taurate monomer;
    1% to 10% by weight silicone oil;
    90% to 98% by weight water; and
    0.1% to 3% by weight clay.

2. The emulsion of claim 1 wherein the Gemini surfactant is disodium ethylene dicocamide PEG-15 disulfate.

3. The emulsion of claim 1 wherein the silicone oil consists of dimethicone.

4. The emulsion of claim 1 wherein the silicone oil is selected from the group consisting of dimethicone, dimethiconol, ethoxylated dimethicone, amodimethicone and derivatives thereof, alkyl substituted dimethicone derivatives, phenyl trimethicone and combinations thereof.

5. The emulsion of claim 1 wherein the clay comprises water-washed smectite clay.

6. The emulsion of claim 5 wherein the clay comprises magnesium aluminum silicate.

7. The emulsion of claim 1 wherein clay is present in the amount of 0.5% to 2% by weight of the emulsion.

8. The emulsion of claim 1 having a viscosity of less than 5000 centipoise.

9. The emulsion of claim 1 further comprising a preservative.

10. The emulsion of claim 1 wherein the gum consists of xanthan gum and guar gum.

11. The emulsion of claim 1 wherein the gum is selected from the group consisting of xanthan gum, guar gum, gellan gum, acacia gum, cellulose gum, dehydroxanthan gum, sclerotium gum, locust bean gum and combinations thereof.

12. A wet wipe comprising:
    a substrate having an emulsion deposited thereon, the emulsion comprising:
        a Gemini surfactant only present in the oil phase or a glucoside-based emulsifier;

a gum blend comprising a gum and propylene glycol alginate, wherein the gum blend is less than or equal to 0.5% weight of the emulsion;
a polymeric rheology modifier comprising an acryloyldimethyl taurate monomer;
1% to 10% by weight silicone oil;
90% to 98% by weight water; and
0.1% to 3% by weight clay.

13. The wet wipe of claim 12 wherein the gum is selected from the group consisting of xanthan gum, guar gum, gellan gum, acacia gum, cellulose gum, dehydroxanthan gum, sclerotium gum, locust bean gum and combinations thereof.

14. The wet wipe of claim 12 wherein the silicone oil is selected from the group consisting of dimethicone, dimethiconol, ethoxylated dimethicone, amodimethicone and derivatives thereof, alkyl substituted dimethicone derivatives, phenyl trimethicone and combinations thereof.

15. The wet wipe of claim 12 wherein the clay comprises water-washed smectite clay.

16. The wet wipe of claim 12 further comprising behenyl alcohol, glyceryl stearate and glycerol stearate citrate.

17. The wet wipe of claim 12 wherein the gums are xanthan gum and guar gum, and the silicone oil is dimethicone.

18. The wet wipe of claim 17 wherein the substrate is a non-woven material.

19. The wet wipe of claim 12 wherein the substrate comprises woven fabric, spunbond fabric, meltblown fabric, knit fabric, wet-laid fabric, scrims or needle-punched webs.

\* \* \* \* \*